US005166525A

United States Patent [19]

Rodgers et al.

[11] Patent Number: 5,166,525

[45] Date of Patent: Nov. 24, 1992

[54] THROUGH THE WAFER OPTICAL TRANSMISSION SENSOR

[75] Inventors: Edward G. Rodgers, Palo Alto; Ottavio T. Rotondale, Belmont, both of Calif.

[73] Assignee: Xinix, Inc., Santa Clara, Calif.

[21] Appl. No.: 653,622

[22] Filed: Feb. 11, 1991

[51] Int. Cl.[5] .......... H01L 21/306

[52] U.S. Cl. .......... 250/338.1; 250/341

[58] Field of Search .......... 250/338.1, 341, 358.1; 156/626, 627, 640, 645

[56] References Cited

U.S. PATENT DOCUMENTS

| | | | |
|---|---|---|---|
| 3,475,242 | 10/1969 | Radimer | 156/626 |
| 4,569,717 | 2/1986 | Ohgami et al. | 156/626 |
| 4,767,495 | 8/1988 | Nishioka | 156/626 |
| 4,851,311 | 7/1989 | Millis et al. | 156/626 X |
| 5,032,217 | 7/1991 | Tanaka | 156/640 |

*Primary Examiner*—Constantine Hannaher
*Assistant Examiner*—Edward J. Glick
*Attorney, Agent, or Firm*—William Green & Associates

[57] ABSTRACT

A device for the optical measurement of light transmitted through silicon wafers and other media during the manufacture of electronic components and particularly during processing within a spray environment. The device is characterized by being a stationary assembly designed to provide structurally inherent optical alignment and focus. In addition the device is provided with a geometry specifically designed to direct any condensate flow away from the surface of the wafer, and with surface characteristics which minimize droplet separation from the surface of the device within a spray environment. The device is designed to permit its location out of the main spray pattern. The light source of the device is made as small as possible to minimize intrusion into the process environment.

7 Claims, 3 Drawing Sheets

THROUGH THE WAFER OPTICAL TRANSMISSION SENSOR

FIELD OF THE INVENTION

This invention relates generally to the use of optical devices to sense the progress of processes, transmit signals related to such processes, detect such signals and extract form such signals information to control such processes. More particularly, this information relates to an optical sensing device which may be used for monitoring the full-process cycle of a wafer in a spray environment.

BACKGROUND OF THE INVENTION

A typical process in which this invention would be used would be the treatment of a silicon wafer to remove selected portions of a metal layer, exposing the silicon substrate. silicon substrates are known to be transmissive to light at certain wavelengths. Therefore, a light source may be directed toward the silicon wafer on one side and a detector positioned on the other side. The light transmitted through the wafer changes as the metal layer is removed and signals proportional to such changes are detected and utilized to determine such changes and to control the process, such as by signalling the endpoint of the process.

In prior art embodiments of apparatus to control etching and etching endpoints in wet etching systems a source optical assembly is mounted upon a moveable arm which extends into an etching chamber. The assembly must be movable so that it can be retracted during certain steps of the process, for example during the removal of the wafer from the etching chamber. Otherwise the bulkiness of the assembly causes it to intrude into the spray environment and interfere with the process. However, the moving of the assembly requires that it be repositioned when it is returned to the chamber and such removal and repositioning generally requires auxiliary motors and software for that purpose. For these reasons the use of such apparatus is not widespread.

This device is designed for incorporation in existing wet process semi-conductor etchers, (such as the 9100 series, manufactured by Applied Process Technologies) or for the replacement of prior art movable assemblies.

SUMMARY OF THE INVENTION

The principal objective of this invention is to provide a through the wafer optical transmission device that is not required to be movable and may be fixedly positioned within a wafer processing spray environment.

Another objective of this invention is to provide a through the wafer optical transmission device which utilizes a method of detection that permits a compactness of design to minimize the intrusion of the optical assembly into the spray environment.

Still another objective of this invention is to provide a through the wafer optical transmission device with optical alignment and focusing inherent in the design thus eliminating the need to optically align and focus the device after manufacture and/or during installation on process equipment.

A further objective of this invention is to provide a the wafer optical transmission device with a geometry specifically designed to direct any condensate flow away from surface of the wafer.

Yet another objective of this invention is to provide a through the wafer optical transmission device with surface characteristics which minimize droplet separation within a process spray environment.

An essential step in processing of thin-film metal layers from silicon wafers during the manufacture of electronic components involves the removal of selected portions of the metal layer and exposure of the silicon substrate which is transmissive at the wavelength of the light source. Although the specifice embodiment and discussion of this invention will be directed toward processing silicon wafers, the process is not limited to silicon wafers but is applicable generally to optical sensing by transmission of light through media during processing.

The practice of a preferred embodiment of this invention consists of directing a light source toward one side of a silicon wafer test sample having a detector located on the opposite side of said test sample.

The light source is selected so that it is weakly or not at all transmitted by the portion of the test sample which is removed during the processing. A Light Emitting Diode with maximum emission at 1300 nm and a refractive lens set at approximately its focal length from the electro-optic active emitter constitutes a suitable light source. The refractive lens is used to direct the light source toward the test sample. The light source is positioned approximately 7 inches above the material to be tested.

The light which is transmitted through the material is collected by a detector. The detector is located approximately 1 inch below the wafer and consists of a refractive lens set at approximately its focal length from the electro-optic active material, which in this embodiment is contained in a Germanium photodiode.

In the embodiment described herein, the light source and the detector are contained in a unitary arm assembly having a portion containing the detector positioned proximate and below the sample and a portion containing the light source positioned distal and above the sample. The terms distal and proximate as used herein are with reference to positions relative to the sample. The distal portion of the arm assembly is curved in an arc selected to allow the positioning of the light source substantially directly above the sample, yet to minimize the intrusion of the arm assembly into the path of the spray during spray treatment of the sample and to inhibit the falling of drops of processing fluid from the arm assembly to the sample. The arm assembly is provided with attachment means for attaching it to an existing structure of the processing equipment. The assembly and its components are positioned and predimensioned with respect to the size of the processing chamber and the location of the sample so that when it is attached it is optically aligned and focused and does not require further focusing or adjustment.

The portion of the arm assembly which is located above the plane of the sample is entirely smooth and substantially continuous. This smoothness in combination with the selected curvature of the distal portion of the arm causes any process fluids which may accumulate upon the arm to flow upon the surface of the arm and eventually be carried by gravity to the area of the attachment means. The attachment means is spaced apart from the sample. This inhibits and minimizes drops of fluid formed upon the arm from falling to the sample.

The requirement that the source be located out of the spray pattern, the limited space available for such a source, and the desire to minimize the intrusion of the device into the space above the wafer, makes it desirable to minimize the size of the source. A small source, utilizing a parallel path would illuminate a relatively small area and might not provide sufficient light for purposes of transmission and detection through the sample. Accordingly to achieve the inconsistent objectives of a small source on the one hand and illumination of a larger detection area (100 square mm or more) on the other hand, the preferred embodiment uses a divergent source.

In the practice of this invention a detected area of approximately 100 square mm is achieved using a 4.2 mm O.D. plano-convex lens at the source and a 16 mm O.D. bi-convex lens at the detector.

DETAILED DESCRIPTION

Figure 1:
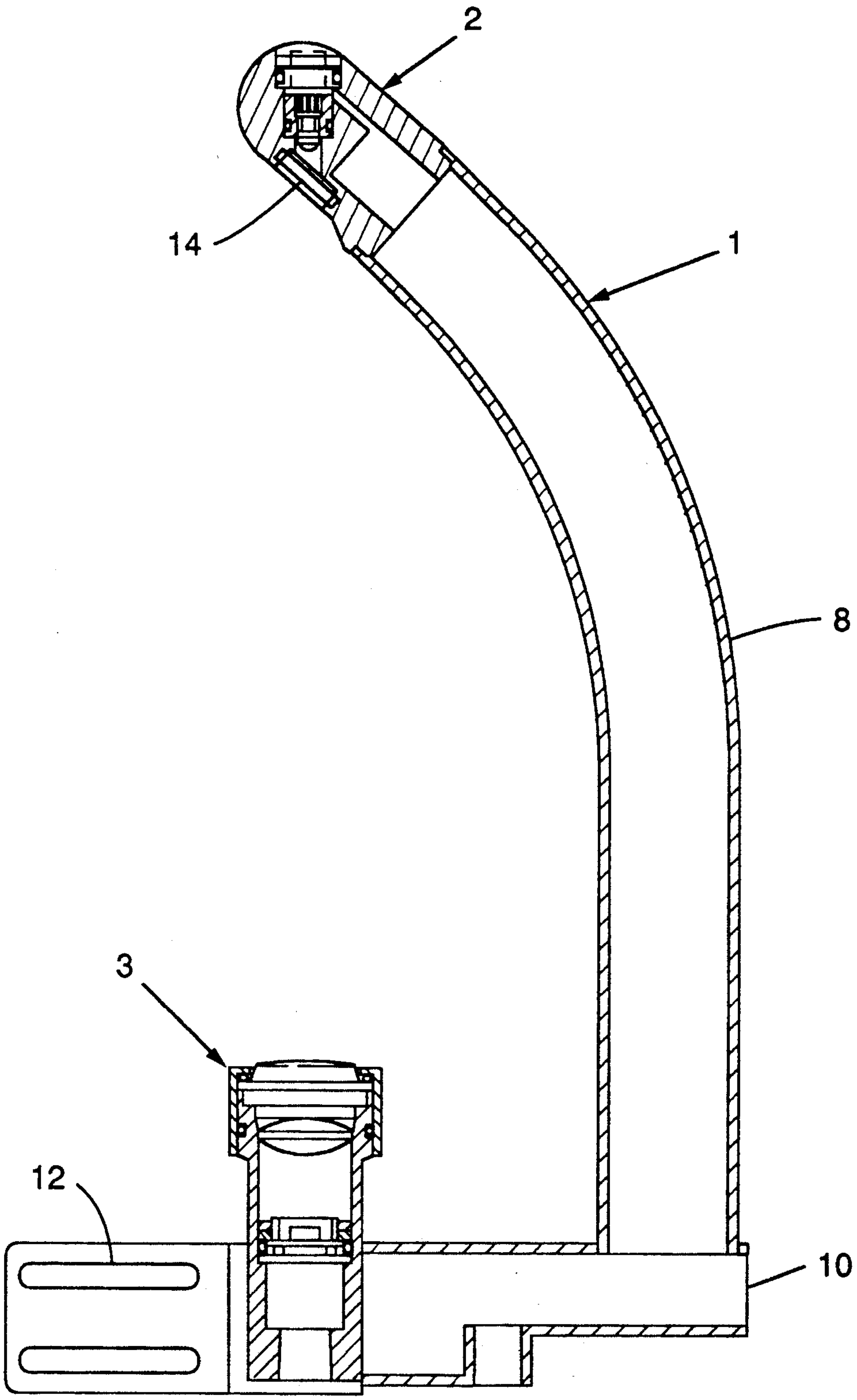
FIG. 1 is a cross-sectional view of the complete device of this invention.

FIG. 1 shows a through the wafer optical transmission sensor in accordance with this invention, generally designated as 1. Sensor 1 has a source opto-electronic assembly 2 located in its distal portion and a detector assembly 3 located in its proximal portion.

Source assembly 2 fits within a cylindrical curved upright tube 8 which terminates in a housing 10 adapted for affixing sensor 1 inside an etching chamber (not shown). Housing 10 is adapted to receive and affix detector assembly 3 by fastening means 12.

Sensor 1 at its distal portion has a window 14 made of material such as quartz, which will transmit light at the frequencies used in the operation of said sensor 1. Tube 8 is made of a material, such as stainless steel which is highly polished to provide a smooth surface and has a curvature which is designed to cause condensation to flow upon its surface and gravitate toward housing 10.

Figure 2:
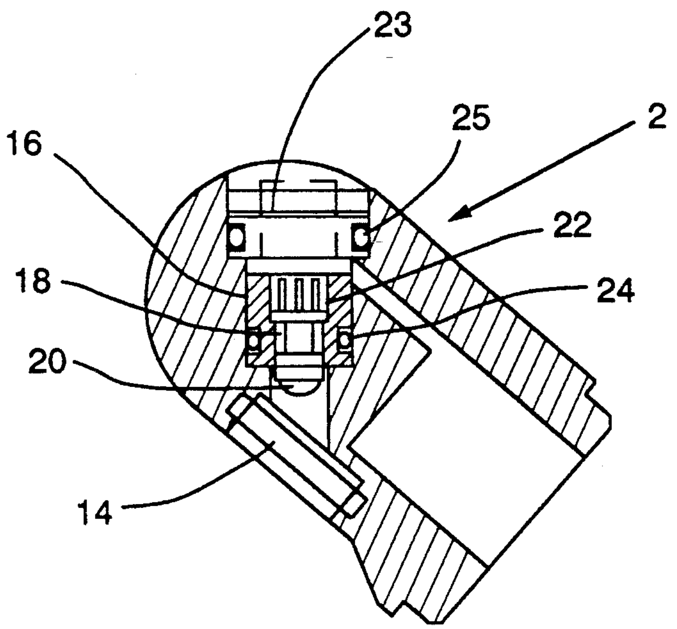
FIG. 2 is a cross-sectional view of the distal portion of the device containing the light source sub-assembly.

FIG. 2 shows source assembly 2 comprising capsule 16 containing LED 18, lens 20, retaining plug 22 and o-ring 24. Lens 20 is positioned so that light passing through said lens 20 is directed toward source window 14. A cap 23, sealed with an o-ring 25 is provided to seal the assembly.

Figure 3:
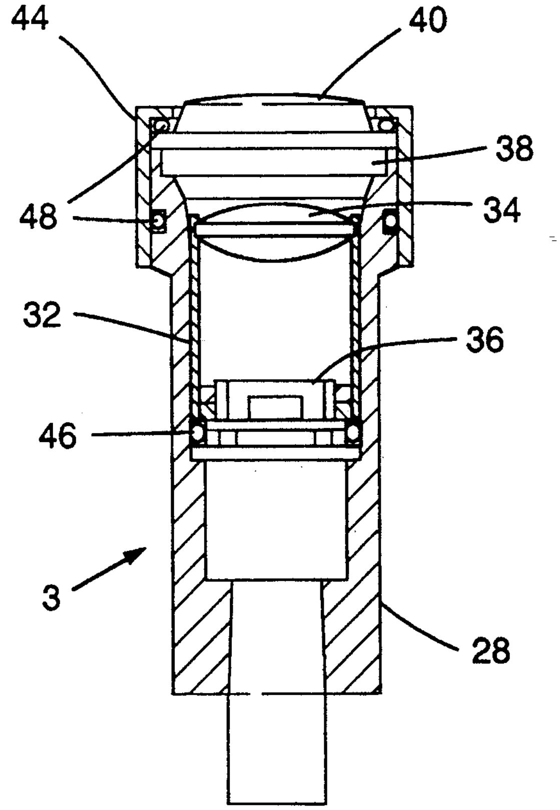
FIG. 3 is a cross-sectional view of the proximate portion of the device containing the detector sub-assembly.

FIG. 3 shows detector assembly 3 which as shown in FIG. 1 is vertically positioned within housing 10. Detector assembly 3 comprises a cylindrical detector tube 28 having a bore within which detector capsule 32 is positioned. Capsule 32 consists of detector lens 34 and germanium detector 36. Lens 34 and detector 36 are spaced apart and axially aligned with each other and with light filter 38 and detector window 40 so that light generated by source assembly 2 which is transmitted through the sample passes consecutively through window 40, and optical filter 38, selected to transmit the source wavelengths and to reject ambient light, lens 34 and ultimately impinges upon detector 36 to generate a signal. nI a manner generally known to those skilled in the art, the signal is carried through tube fitting by electrical connections, not shown, to a signal amplifier, measured and interpreted. A Xinix Model 2200 Controller would be suitable for this purpose.

A tube cap 44 designed to fit over the top of detector tube 28, and to seal the assembly with the aid of o-rings 48 caps the assembly. Another o-ring 46 is used to seal detector capsule 32 within detector tube 28.

We have found that for a silicon substrate the preferable source wavelength would be in the region of high transmission beyond 1100 nm (wavelengths longer than 1100 nm). In the described embodiment a 1300 nm source was selected. For other substrates (e.g. gallium arsenide and derivatives) different wavelengths, chosen so that the material which is illuminated and not removed during the process will transmit, may be selected. The determination of such wavelengths is within the skill of the art and the use of different wavelengths is within the scope of this invention.

Although the specific example of the invention described herein positions the light source above the wafer and the detector below the wafer, these positions could be reversed without departing from the teaching of the invention.

Figure 4:
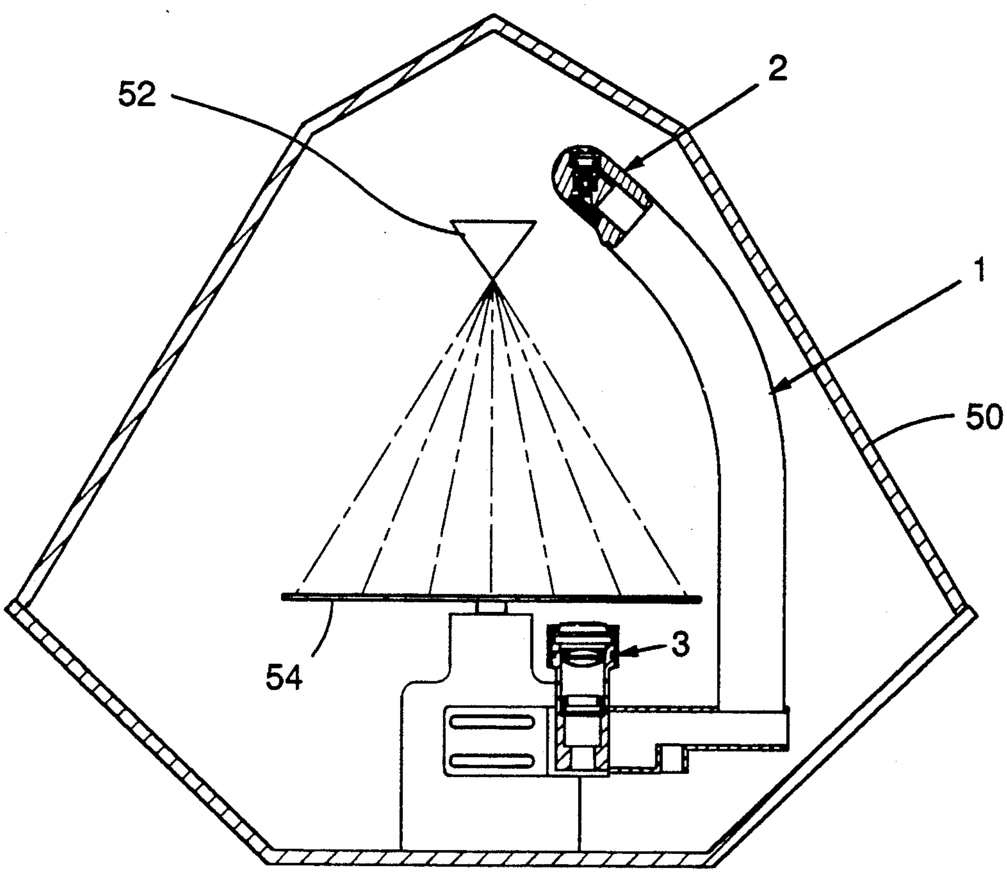
FIG. 4 illustrates the device positioned within a process chamber.

FIG. 4 illustrates sensor 2, in accordance with the preferred embodiment of this invention, positioned within a typical process chamber 50. Spray source 52 directs a spray to impinge upon a wafer 54. As the drawing shows, sensor 2 is located above, but out of the pattern of the spray, in a position which allows the source assembly 2 to direct light through wafer 54 to detector assembly 4.

The assembly as depicted in the preferred embodiment is a unitary assembly. However, if desirable, the source assembly could be one unit separately affixed to one portion of a process chamber and the detector assembly could be another unit affixed to another portion of the assembly. Obviously, both assemblies would be positioned to transmit light through a sample as taught in the invention. Such an approach might be appropriate where space within the process chamber is limited or where it is desireable to further limit intrusion into the process chamber.

The invention as shown is also designed so that the sensor unit and the detector unit are each contained within capsules. If the process or the media to be processed are changed and it is desirable to modify the optics, the source frequency, or other characteristics of the signal transmission and detection, the capsules may be removed, the components modified appropriately and the capsules reinstalled within the assembly.

Although the invention has been particularly shown and described with respect to a preferred embodiment, those skilled in the art will understand that changes in form and detail to the embodiments shown and described herein may be made without departing from the spirit and scope of the invention.

We claim:

1. Apparatus for optically sensing light transmitted through media during processing of said media within wet etching chambers comprising:

an assembly adapted for fixed attachment to and within said wet etching chambers, said assembly consisting of (a) a light source assembly containing a light source for emitting light at a pre-selected wavelength, a window to permit light generated by said light source to exit said light source assembly, and lens for directing the light emitted from said light source toward said media; and (b) a detector assembly, containing a window positioned to receive light transmitted through said media, optical filter means selected to transmit the light generated from the source and passing through said media and to reject ambient light, and detector means for collecting said transmitted light and transmitting signals generated by said light to signal processing means for controlling said wet etching process.

2. The apparatus of claim in which said assembly is a unitary assembly and is polished and shaped to minimize droplet separation within a spray environment and to direct condensate developed during spraying away from said media.

3. The apparatus of claim 1 in which said media is a silicon substrate wafer having thin-film metal layers and said processing is the removal of selected portions of thin film metal layers from said silicon wafer to expose said silicon substrate.

4. The apparatus of claim 1 in which said light source is selected to transmit light at a wavelength greater than 1100 nm.

5. The apparatus of claim 1 in which said light source is selected to transmit light at the wavelength of 1300 nm.

6. The apparatus of claim 1 in which said process includes a spray step and said light source assembly is positioned substantially outside of the spray pattern generated by the spray step.

7. In a method for controlling the manufacture of devices which manufacture includes the step of wet eching within a chamber a material having a metal layer to remove selected portions of said metal layer and determining the extent of removal of said metal layer the combination of directing a light beam through said material and detecting the light transmitted through said material using apparatus positioned within said wet etching chamber and remaining in such chamber during the wet etching process, the following steps fixedly positioning a unitary assembly within said wet etching chamber said assembly consisting of a distal portion positioned above said material and substantially out of the wet etching spray pattern, containing a light source for emitting light at a pre-selected wavelength, a window to permit light generated by said light source to exit said distal portion of said assembly, and lens for directing said light source toward said material; and a proximal portion positioned below said material, containing a window positioned to receive light transmitted through said material, optical filter means selected to transmit the light generated from the source and passing through said material and to reject ambient light, and detector means for collecting said transmitted light and transmitting signals generated by said light to signal processing means for controlling said wet etching process.

* * * * *